United States Patent [19]

Sears

[11] Patent Number: 4,534,899

[45] Date of Patent: Aug. 13, 1985

[54] SYNTHETIC PHOSPHOLIPID COMPOUNDS

[75] Inventor: Barry D. Sears, Marblehead, Mass.

[73] Assignee: Lipid Specialties, Inc., Danvers, Mass.

[21] Appl. No.: 472,481

[22] Filed: Mar. 7, 1983

Related U.S. Application Data

[63] Continuation-in-part of Ser. No. 284,675, Jul. 20, 1981, Pat. No. 4,426,330.

[51] Int. Cl.³ ............................................. C07F 9/10
[52] U.S. Cl. ..................................... 260/403; 260/944
[58] Field of Search ............................... 260/403, 944

[56] References Cited

U.S. PATENT DOCUMENTS

| | | | |
|---|---|---|---|
| 2,310,679 | 2/1943 | De Groote et al. | 260/403 X |
| 3,085,100 | 4/1963 | Chang | 260/403 |
| 3,542,820 | 11/1970 | Rakhit | 260/403 |
| 3,577,446 | 5/1971 | Rakhit | 260/403 |
| 4,016,100 | 4/1977 | Suzuki et al. | 252/316 |
| 4,086,257 | 4/1978 | Sears | 260/403 |
| 4,159,988 | 7/1979 | Eibl et al. | 260/403 X |
| 4,215,064 | 7/1980 | Lindemann et al. | 260/403 |
| 4,261,911 | 4/1981 | Lindemann et al. | 260/403 |

FOREIGN PATENT DOCUMENTS

| | | | |
|---|---|---|---|
| 2756866 | 6/1979 | Fed. Rep. of Germany | 260/403 |
| 727655 | 4/1980 | U.S.S.R. | 260/403 |

OTHER PUBLICATIONS

Wren et al., CA 63: 13066, (1965).
Rehbinder et al., *Index Chemicus*, 17, 50791, (1965).
Szogyi et al., CA 96:129747k, (1982).

*Primary Examiner*—Thomas A. Waltz
*Attorney, Agent, or Firm*—Richard P. Crowley

[57] ABSTRACT

Synthetic phospholipid compounds and their method of preparation, which compounds are phosphatidylethanolamine polycarboxyl polyalkylene glycols and are prepared by the reaction of a phosphatidylethanolamine, a polycarboxylic acid, such as succinic or glutaryl anhydride, and a polyalkylene glycol, such as polyethylene glycol.

18 Claims, No Drawings

SYNTHETIC PHOSPHOLIPID COMPOUNDS

REFERENCE TO PRIOR APPLICATION

This application is a continuation-in-part of U.S. patent application Ser. No. 284,675, filed July 20, 1981, now U.S. Pat. No. 4,426,330, issued Jan. 17, 1984, hereby incorporated by reference.

BACKGROUND OF THE INVENTION

Phospholipids, such as lecithin, are amphipathic compounds in that they consist of both hydrophobic and hydrophilic groups or regions within the same molecule. The balance between these hydrophobic and hydrophilic regions determines their physical properties in an aqueous environment. The uses of natural phospholipids as additives are numerous in the food industry (for example, as emulsifiers), in cosmetics, for industrial uses and for the pharmaceutical industry, especially in the preparation of drug-delivery systems. U.S. Pat. Nos. 4,086,257; 4,097,502; 4,145,410; and 4,159,988 disclose various modifications of the polar-head-group region of natural phospholipids which lead to unique and unexpected physical properties.

Further, various derivatives of lecithin are known, such as, for example, oxyalkylated lecithin compounds (see U.S. Pat. Nos. 3,085,100 and 2,310,679) and phosphatidylalkanolamine derivatives (see, for example, U.S. Pat. Nos. 2,801,255; 3,542,820; 3,577,466; and 4,254,115). It is desirable to provide novel, synthetic phospholipids, particularly having enhanced solubility and surfactant properties in an aqueous environment, especially for the formulation of water-insoluble materials, such as drugs or cosmetic ingredients, within an aqueous environment.

The parent application describes novel, synthetic phospholipid compounds, such as phosphatidylalkanolamine carboxyl polyalkylene glycol like phosphatidylethanolamine carboxyl polyethylene glycol compounds. These novel compounds are prepared by the covalent reaction of a carboxylic analog of the polyalkylene glycol with the phosphatidylalkanolamine, to provide novel, biodegradable, phospholipid compounds which contain an amide linkage.

SUMMARY OF THE INVENTION

This invention relates to novel, improved, phospholipid compounds and to the method of preparation and to the use of such compounds, particularly in solubilizing, in an aqueous environment, water-insoluble compounds.

The invention describes a new, improved series of phospholipid compounds in which the polar-head-group region is modified by the covalent attachment through two or more carboxylic groups of polyalkylene glycols. The novel, synthetic phospholipid compounds of the invention are phosphatidylalkanolamine polycarboxyl polyalkylene glycol compounds, such as phosphatidylethanolamine di or tri carboxyl polyethylene and polypropylene glycol compounds. The phospholipids of the invention are analogs of the phospholipid compounds of the parent application. This invention also provides a different and improved method of coupling the polyalkylene glycol polymer to the phospholipid. The phospholipid compounds of the invention, like the compounds of the parent application, have enhanced surfactant properties, are soluble in acetone and are biodegradable.

The phospholipids of the invention are represented by the following structural formula:

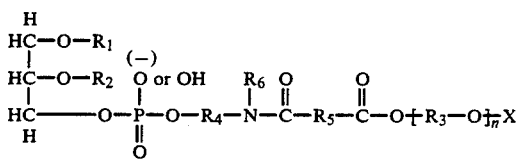

wherein:
(a) $R_1$ and $R_2$ represent hydrogen or saturated or unsaturated, straight or branch-chain acyl groups, such as organic acyl radicals having 2 to 24 carbon atoms; for example, $C_2$ to $C_{20}$ fatty-acid radicals, such as oleic, stearic, linoleic, linolenic, palmitic, myristic or arachidonic acid, or may be derived from natural products, such as plants like soybean or egg;
(b) $R_3$ represents an alkylene radical, such as a $C_2$ to $C_4$ group like ethylene, propylene or butylene; that is, tetramethylene;
(c) $R_4$ represents a polymethylene radical, typically a $C_2$ to $C_{10}$ polymethylene divalent radical, and particularly an ethylene radical; that is, a dimethylene radical, as in natural lecithin, or a propylene radical; that is, a trimethylene radical;
(d) $R_5$ represents an organic linking radical; for example, a hydrocarbon radical, of from about 1 to 24 carbon atoms, but typically from about 2, 3 or 4 carbon atoms, which radical may be saturated or unsaturated, may be substituted, for example, with hydroxyl, amino or carboxyl groups, or be an unsubstituted radical, such as a polymethylene (—$CH_2$—) radical like an ethylene, propylene or butylene radical;
(e) $R_6$ represents hydrogen or an alkyl, such as methyl, radical;
(f) X represents hydrogen or an alkyl radical, typically a lower alkyl radical like a $C_1$ to $C_4$ alkyl group, such as a methyl radical; and
(g) n represents a number of the alkylene oxide groups and may vary from 0 to about 200 or more; for example, from about 2 to 100, such as 2 to 20, to provide phospholipids having, for example, a molecular weight of from 150 to 3000 or more; for example, 200 to 2000.

One particular group of phospholipids of the invention prepared by the use of succinic or glutaric anhydride, or other dicarboxylic acids, would be represented by the structural formula:

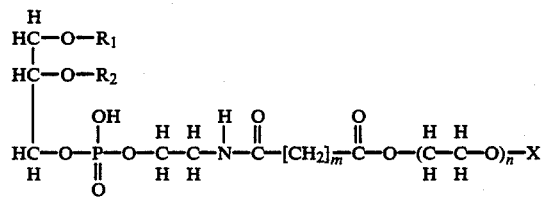

wherein m represents a number of 1, 2, 3 or 4.

The polycarboxylic acids used in the preparation of the phospholipid compounds are preferably cyclic acids and more particularly cyclic acid anhydride compounds for ease of reaction; for example, $C_3$ to $C_6$ dicarboxylic acids, particularly which form 4-to-7-member-ring anhydrides, such as succinic acid, glutaric acid, adipic acid and phthalic anhydride. Suitable carboxylic acids include, but are not limited to, aliphatic, cycloaliphatic, di and tri carboxylic acids, such as succinic acid, glutaric acid, glutamic acid, citric acid, tartaric acid, oxalic acid, adipic acid, malic acid, maleic acid, as well as long-chain dicarboxylic acid, although waxy, solid compounds may result from the use of long-chain acids. Preferably the acid compounds employed are the $C_3$ to $C_7$ dicarboxylic acid anhydrides. These novel phospholipid compounds have a distinctly different chemical composition than the compound described, for example, in U.S. Pat. Nos. 2,310,679 and 3,085,100, which are products from the coupling of ethylene oxide or similar compounds to crude soy lecithin.

The use of the term "lecithin" describes a number of compounds including lecithin (that is, phosphatidylcholine), a compound that cannot react with ethylene oxide. On the other hand, soy lecithin does contain phosphatidylethanolamine, phosphatidylinositol and a variety of glycolipids. All of these compounds in crude lecithin can react with ethylene oxide or similar compounds containing a reactive cyclooxide group to form various adducts. For example, in phosphatidylinositol and with glycolipids, the reactive groups in these molecules are hydroxyl groups which will form an ether linkage, when reacted with ethylene oxide. Phosphatidylethanolamine, which contains a primary amino group, will react with ethylene oxide to form an alkylamine linkage (see N. Schonfeldt, "Surface Active Ethylene Oxide Adducts", Pergamon Press, 1969). In both cases, these adducts are not biologically degradable, and, therefore, such compounds are undesirable for use in the cosmetic and pharmaceutical industries.

The phospholipids of the invention comprise synthetic phospholipids in which the linkage between the synthetic ethylene oxide or propylene oxide polymer and the naturally occurring phospholipid is a biologically degradable linkage; for example, an amide linkage, which makes these novel phospholipid compounds useful for cosmetics and pharmaceutical uses.

The preparation of the phospholipid compounds is best accomplished by the addition of a cyclic polyacid, particularly anhydride, such as succinic or glutaric acid anhydride, to the polyalkylene oxide polymer. The coupling of the appropriate carboxylic analog of the polyalkylene oxide polymer to the phosphatidylalkanolamine molecule, such as phosphatidylethanolamine, gives the desired compounds. Alternatively, the cyclic acid anhydride can be coupled to the phosphatidylethanolamine, and then the polyalkylene oxide polymer is coupled to the modified phospholipid. For example, in one method the low-cost acidic polyalkylene glycol compound can be admixed with crude soy lecithin for a coupling reaction with the phosphatidylethanolamine, and the novel phospholipid compounds extracted with acetone. The acidic polymer may be converted to an acid halide compound, to increase the speed of the reaction. The acidic polyalkylene glycol polymer compound can be purified further via distillation, ion-exchange chromatography or absorption chromatography. The acyl analog of the polyethylene oxide polymer is activated by a convenient activating agent, such as oxalyl chloride or 1,1 carbonyl diimidazole. The activated carboxylic derivative of the parent polyalkylene oxide polymer is then coupled to the phosphatidyletha-nolamine via an amide linkage, to form the phospholipid analog compounds of this invention.

The phosphatidylethanolamine either can be isolated from natural sources, synthesized according to established chemical procedures, or enzymatically synthesized using the corresponding phosphatidylcholine compound in the presence of ethanolamine and phospholipase D. The reaction of the phosphatidylethanolamine and the carboxylic derivative of the polyalkylene oxide polymer is carried out in an inert solvent. The progress of the reaction can be monitored by thin-layer chromatography. Purification of the final product, if necessary, may be carried out using column chromatography.

In the phospholipid compounds of this invention, the polar-head group of the phosphatidylethanolamine has been modified to alter its physical properties, by the inclusion of a polyalkylene oxide polymer. In all cases where natural phospholipids can be used, such as in drug-delivery systems, in cosmetics, in food, in industrial uses, in treating atherosclerosis, for intravenous nutrition and other uses, these new synthetic phospholipid compounds can be used alone or in combination with other natural phospholipids, especially phosphatidylcholine. Biologically these synthetic phospholipids will be immunologically inert. For example, polyethylene oxide polymers attached to proteins are nonimmunogenic and well tolerated by the body (see Abuchowski et al, J. Biol. Chem. 252, pp 3578–3581 (1977)). The covalent linkage between a typical polyalkylene example, such as polyethylene oxide polymer and the phosphatidylethanolamine, is biologically degradable, and phosphatidylethanolamine, itself, is a natural compound.

As a result, these novel compounds have utility in encapsulating drugs, especially water-insoluble drugs, as drug-delivery systems that either can be administered orally or via injection, such as in the encapsulation process disclosed in corresponding U.S. Ser. No. 90,994, filed Nov. 13, 1979, now U.S. Pat. No. 4,320,121, issued Mar. 16, 1982, as well as in the method of U.S. Pat. No. 4,016,100, both hereby incorporated by reference.

The presence of the hydrophilic alkylene oxide polymer, particularly the polyethylene oxide polymer moiety in the phospholipids, also gives rise to novel and unexpected physical properties in an aqueous environment. As an example, unsaturated phosphatidylethanolamines, especially those isolated from soybeans, do not form any stable type of structure in water. Phosphatidylcholine, if hydrated with an aqueous solution, forms large (>2000 Å) structure termed multilamellar liposomes. On the other hand, gangliosides have a similar hydrophobic region, compared to phosphatidylethanolamine and phosphatidylcholine, but the polar region of the ganglioside molecule is composed of hydrophilic oligiosaccharides. The presence of these oligiosaccharides allows the ganglioside to organize into a stable micelle upon hydration with water. By covalently attaching a hydrophilic polyalkylene polymer, such as polyethylene or polypropylene oxide polymers, to phosphatidylethanolamine, a phospholipid analog to ganglioside is essentially synthesized. It also should be noted that, while no molecular species of phosphatidylethanolamine will form a stable structure in an aqueous environment, the phospholipid analog compounds described herein do form stable structures upon hydration. As a consequence of this physical behavior, a variety of water-insoluble compounds can be formulated in a stable form in an aqueous environment at physiological pH. Furthermore, the spontaneous structure that these phospholipids form, when hydrated with water from the dry state, is small (less than 200 Å; for example, typically average 75 to 100 Å), which results in an optically clear solution.

The actual organization of these structures, however, will depend, at least in part, on the selected acyl chain composition of the phosphatidylethanolamine and the alkylene oxide polymer. In particular, with phosphatidylethanolamine isolated from soybeans and various polyethylene oxide polymers, micellar structures of less than 200 Å diameter are spontaneously and easily formed, upon addition of water to the dried phospholipid analog. These structures are distinct and unique, as compared to liposomes or other lipid vehicles that are composed of phosphatidylcholine.

For the purpose of illustration only, the invention will be described in connection with the method of preparation and use of certain compounds; however, it is recognized that various changes and modifications to the illustrated examples can be made by those persons skilled in the art, all falling within the spirit and scope of the invention.

DESCRIPTION OF THE EMBODIMENTS

EXAMPLE 1

Soy phosphatidylethanolamine succinyl polyethylene glycol monomethyl ether (molecular weight 252)

Succinyl polyethylene glycol monomethylether compounds were prepared in accordance with and under the following general method and conditions. 1 mole of the polyethylene glycol polymer was heated with 5 moles of finely divided succinic anhydride in a slurry of $CCl_4$ under a nitrogen atmosphere. The solution was magnetically stirred and heated overnight at 75° C. under a nitrogen atmosphere. Temperature control is important, as the reaction mixture darkens above 75° C. Upon cooling to room temperature, the excess succinic anhydride was removed by filtration. The reaction mixture was then dissolved in a 1:1 methylene chloride/methanol mixture, and sufficient concentrated $NH_4OH$ was added, so that an aliquot of the reaction mixture was approximately pH 9, when diluted with water. The succinyl polymer reaction mixture was dissolved in a 95:5:0.8 mixture of methylene chloride/methanol-concentrated $NH_4OH$ and applied to a silicic acid column equilibrated in the same solvent. The succinyl polymer was eluted with a step gradient of increasing methanol content. The purity of the fraction was monitored by thin-layer chromatography, using a solvent system of 90:10:1 of methylene chloride/methanol-concentrated $NH_4OH$. Pure fractions of the succinyl polymer were evaporated to near dryness. Sufficient HCl was added to the mixture, so that an aliquot, when diluted with water, gave a pH of between 2 and 2.5. The compound was then evaporated to dryness. Methylene chloride was added to the dried material, and any particulate material was filtered off. The filtrate was evaporated to dryness and dried overnight under high vacuum.

The above conditions were used to make the succinyl polyethylene glycol monomethylether, using, as the starting material, polyethylene glycol monomethylether with a molecular weight of 252. To 2200 μmoles of the succinyl polymer compound were added 2000 μmoles of 1,1 carbonyl diimidazole in a benzene solution. The solution was heated at 60° C. for 10 to 15 minutes, until the bubbling had ceased. This solution was transferred to another flask containing 1000 μmoles of dried soy phosphatidylethanolamine (PE), which was prepared by the enzymatic conversion of soy phosphatidylcholine using ethanolamine and phospholipase D from Savoy cabbage. Sufficient benzene was added to ensure that all of the soy PE had dissolved. Then most of the benzene was removed, leaving a thick slurry. This slurry was stirred with a magnetic stirrer for approximately 6 hours at 70° C. under a nitrogen atmosphere. The extent of the conversion of PE to the desired product was monitored by thin-layer chromatography. The reaction mixture was taken to dryness and then partitioned into a two-phase Folch System, with 0.2M HCl in the upper phase. The lower phase was extracted four more times with this acidic Folch upper phase, and twice with a 0.3M $NH_4$ acetate upper phase, to remove the imidazole and excess noncoupled succinyl polymer compound. The lower phase was evaporated to dryness. The sample was dissolved in 95:5:0.8 methylene chloride/methanol-concentrated $NH_4OH$ and applied to a silicic acid column equilibrated in the same solvent. The soy PE-succinyl polyethylene glycol monomethylether (molecular weight 252) was eluted with a step gradient of increasing methanol content, while maintaining approximately 0.8 to 1.0 concentrated $NH_4OH$ in the eluting solvent. The elution profile was monitored by thin-layer chromatography, using 80:2:1 methylene chloride/methanol-concentrated $NH_4OH$ as the solvent. Pure fractions of the product were pooled and reduced to dryness. The pH was tested and adjusted, if needed, to between 5 to 7. The compound was then dissolved in methylene chloride. The yield of the product was 35% based on the starting soy PE content.

EXAMPLE 2

Soy phosphatidylethanolamine succinyl polyethylene glycol monomethylether (molecular weight 120)

A succinyl polyethylene glycol monomethylether (molecular weight 120) polymer compound was prepared as described in Example 1. 7500 μmoles of the succinyl polyethylene glycol were dissolved in benzene and 4000 μmoles of 1,1 carbonyl diimidazole were added. The solution was heated at 60° C., until all bubbling had ceased. The solution was added to 1000 μmoles of soy PE that previously had been dried under high vacuum. The reaction conditions were the same as in Example 1. The yield of the pure product, after column chromatography, was 42%.

EXAMPLE 3

Soy phosphatidylethanolamine succinyl polyethylene glycol monomethylether (average molecular weight 1900)

A succinyl polyethylene glycol monomethylether (average molecular weight 1900) was prepared as described in Example 1. 1750 μmoles of this compound were dissolved in benzene and 1000 μmoles of 1,1 carbonyl diimidazole were added. The solution was heated to 60° C., until the bubbling had ceased. The solution was added to 483 μmoles of dried soy PE. The reaction conditions were as described in Example 1. The yield of column-purified material was 44%.

EXAMPLE 4

Soy phosphatidylethanolamine succinyl polyethylene glycol monomethylether (average molecular weight 350)

A succinyl polyethylene glycol monomethylether (average molecular weight 350) was prepared as described in Example 1. 7000 μmoles of succinyl polyethylene glycol monomethylether compound were dissolved in benzene and 4000 μmoles of 1,1 carbonyl diimidazole were added. The solution was heated at 60° C., until the bubbling had ceased. This solution was added to 1050 μmoles of dried soy PE. The reaction conditions to form the product were the same as described in Example 1. The yield of the pure product, after column chromatography, was 70%.

EXAMPLE 5

Soy phosphatidylethanolamine succinyl polyethylene glycol monomethylether (average molecular weight 750)

A succinyl polyethylene glycol monomethylether (average molecular weight 750) was prepared as described in Example 1. 7500 μmoles of the compound were dissolved in benzene and 5000 μmoles of 1,1 carbonyl diimidazole were added. The solution was heated at 60° C., until bubbling had ceased. This solution was then added to 1200 μmoles of dried soy PE. The reaction conditions were then as described in Example 1. The yield of the column-purified product was 52%.

EXAMPLE 6

Soy phosphatidylethanolamine succinyl polyethylene glycol monomethylether (average molecular weight 550)

A succinyl polyethylene glycol monomethylether (average molecular weight 550) was prepared as described in Example 1. 3070 μmoles of the compound were dissolved in benzene and 2000 μmoles of 1,1 carbonyl diimidazole were added. The solution was heated at 60° C., until the bubbling ceased. The solution was added to 1127 μmoles of dried soy PE. The reaction conditions were the same as described in Example 1. The yield of the column-purified material was 58%.

EXAMPLE 7

Soy phosphatidylethanolamine succinyl polyethylene glycol monomethylether (molecular weight 252)

Another method of producing the compounds of the invention is the coupling of succinic anhydride to soy PE and then reacting the modified PE with the appropriate polyethylene glycol polymer. Succinic anhydride (1000 μmoles) was reacted with 1000 μmoles of soy PE in a methylene chloride slurry under a nitrogen atmosphere at 70° C. overnight. The unreacted succinic anhydride was filtered off. The methylene chloride was evaporated and the succinic acid modified PE was purified by column chromatography. 500 μmoles of the succinic acid modified PE was dissolved in benzene, and 500 μmoles of 1,1 carbonyl diimidazole were added. The solution was heated at 60° C., until the bubbling had ceased. 750 μmoles of the polyethylene glycol monomethylether (molecular weight 252) were added to the solution, and the mixture was heated for 3 hours under a nitrogen atmosphere at 70° C. The purified product was then recovered as described in Example 1.

EXAMPLE 8

Soy phosphatidylethanolamine succinyl tetraethylene glycol (molecular weight 194)

The soy PE succinic acid derivative was prepared as described in Example 7. 650 μmoles of the compound were dissolved in benzene and 650 μmoles of 1,1 carbonyl diimidazole were added. The solution was heated at 60° C., until bubbling had ceased. To the solution were added 650 μmoles of tetraethylene glycol. The mixture was heated at 70° C. under a nitrogen atmosphere for 3 hours. The purified product was recovered as described in Example 1. The yield of the column-purified material was 37%.

EXAMPLE 9

Soy phosphatidylethanolamine glutaryl polyethylene monomethylether (molecular weight 252)

One of the disadvantages of using the succinic anhydride as a linking agent is the high melting point of the anhydride that prevents a homogenous reaction mixture. In using glutaric anhydride, many of these disadvantages can be addressed. In particular, 1 mole of the polyethylene glycol was heated with 2 to 3 moles of the glutaric anhydride in a $N_2$ atmosphere at 75° C. in the absence of any solvent. At the end of the reaction as determined by thin-layer chromatography, the reaction mixture was dissolved in methylene chloride/methanol 1:1 (v/v) and recovered as described for the succinyl material as described in Example 1. In this particular example, 7.5 g of polyethylene glycol monomethylether (molecular weight 252) and 5 g of glutaric anhydride were placed in a reaction vessel and heated to 75° C., with magnetic stirring, for 3 hours under a $N_2$ atmosphere. The glutaryl polyethylene glycol compound was purified by column chromatography. 1200 μmoles of 1,1 carbonyl diimidazole were added to 1500 μmoles of the glutaryl polyethylene glycol compound dissolved in benzene. The solution was heated at 60° C., until bubbling had ceased. This solution was added to 1127 μmoles of dry soy PE, and the reaction mixture was heated for 3 hours at 70° C. The mixture was extracted and purified as described in Example 1. The yield of pure product was 67%.

Examples 10–14 illustrate that the phospholipids of the invention and the parent application are useful in solubilizing water-insoluble drugs, oils and fragrances, to provide aqueous solutions.

EXAMPLE 10

The anticancer drug, Taxol (an experimental drug of the National Cancer Institute which inhibits the ability of cells to divide), is insoluble in water. 8 μmoles of Taxol (6.5 mg) were dissolved in methylene chloride with 72 μmoles of soy phosphatidylethanolamine succinyl polyethylene glycol monomethylether (average molecular weight 550). The solution was taken to dryness and pumped on by a high vacuum. The dried material was dehydrated with 1 ml of 10 mM Tris (pH 8.5) and vortexed at room temperature. The resulting solution was optically clear. The solution was then adjusted with concentrated dextrose, to bring the dextrose concentration to 0.3M; thus making the sample suitable for intravenous injection.

EXAMPLE 11

Pentobarbital is a barbituate that is insoluble in water at physiological pH as the acid form. It is the water-insoluble form that exerts its therapeutic activity. A standard solution sodium pentobarbital is stable only at high pH and was adjusted with dilute HCL to pH 3. The precipitated pentobarbital was removed by filtration. 40 μmoles of the pentobarbital were dissolved in methylene chloride with 60 μmoles of the soy phosphatidylethanolamine succinyl polyethylene glycol monomethylether (molecular weight 252). The solution was taken to dryness and then pumped on by high vacuum. The dried material was hydrated with 2 ml of 10 mM Tris (pH 8.5), to form an optically clear solution. The solution was adjusted with concentrated dextrose to give a 0.3M solution suitable for intravenous injection.

EXAMPLE 12

The anticancer drug, hexamethylmelamine, is water-insoluble. 2 mg of hexamethylmelamine and 70 μmoles of soy phosphatidylethanolamine succinyl polyethylene glycol monomethylether (average molecular weight 550) were dissolved in methylene chloride. The solution was taken to dryness and then pumped on by high vacuum. The solution was hydrated with 1 ml of 10 mM Tris (pH 8.5), to give an optically clear solution. The solution was adjusted with concentrated dextose to give a final dextose concentration of 0.3M suitable for intravenous injection.

EXAMPLE 13

Another unique property of the phospholipids of the parent application and of this invention is their ability to act as exceedingly powerful surfactants for cosmetic ingredients, such as oils and petroleum jelly. As an illustration of such ability, 1.6 g of petroleum jelly and 160 mg of soy phosphatidylethanolamine succinyl polyethylene glycol monomethylether (molecular weight 252) were dissolved in hexane and taken to dryness and pumped on at high vacuum. To the dried material were added 4 ml of 10 mM Tris (pH 8.5). The hydrated solution was then sonicated with a Branson W-375 sonifier at 40° C. for 2 minutes. The resulting solution was opaque, but had excellent flow characteristics. When applied to the skin, there was an immediate and noticeable cooling sensation, due to the evaporation of water, and a pleasing tactile sensation.

EXAMPLE 14

Another example of the use of the compounds of the invention in the cosmetic field is the solubilization of water-insoluble fragrance oils in an aqueous environment. For example, 0.250 ml of a fragrance oil and 200 μmoles of soy phosphatidylethanolamine glutaryl polyethylene glycol monomethylether (molecular weight 252) were dissolved in 0.5 ml of ethanol. The solution was then diluted with 40 ml of water. The resulting solution was optically clear and retained the fragrance aroma.

What is claimed is:

1. A synthetic phospholipid compound having the structural formula:

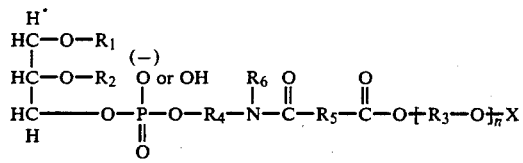

wherein $R_1$ and $R_2$ represent hydrogen or organic acyl radicals; $R_3$ represents a $C_2$ to $C_4$ alkylene radical; X represents hydrogen or an alkyl radical; $R_4$ represents a $C_2$ to $C_{10}$ alkylene radical; $R_5$ represents an organic linking radical; $R_6$ represents hydrogen or a lower alkyl radical; and n represents a number of from 0 to 200.

2. The phospholipid compound of claim 1 wherein $R_1$ and $R_2$ represent $C_2$ to $C_{20}$ fatty-acid radicals.

3. The phospholipid compound of claim 1 wherein $R_5$ represents a polymethylene radical.

4. The phospholipid compound of claim 3 wherein $R_5$ represents a $C_1$ to $C_4$ methylene radical.

5. The phospholipid compound of claim 1 wherein n represents a number of from 2 to 100.

6. The phospholipid compound of claim 1 wherein $R_1$ and $R_2$ are organic radicals derived from soybeans.

7. The phospholipid compound of claim 1 wherein $R_4$ represents an ethylene radical.

8. The phospholipid compound of claim 1 wherein $R_3$ represents an ethylene radical.

9. The phospholipid compound of claim 1 wherein $R_6$ represents a methyl radical.

10. The phospholipid compound of claim 1 wherein the molecular weight is from about 150 to 3000.

11. The synthetic phospholipid compound having the structural formula:

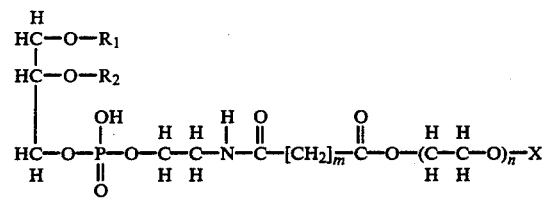

wherein $R_1$ and $R_2$ represent $C_2$ to $C_{20}$ hydrocarbon organic acyl radicals; X represents hydrogen or a methyl radical; m represents a number of from 1 to 4; and n represents a number of from 0 to 200.

12. The synthetic phospholipid compound which is a phosphatidylethanolamine succinyl polyethylene glycol compound.

13. The synthetic phospholipid compound which is a phosphatidylethanolamine glutaryl polyethylene glycol compound.

14. The synthetic phospholipid compound which is a phosphatidylethanolamine di or tri carboxyl polyethylene or polypropylene glycol compound.

15. The synthetic phospholipid compound of claim 14 wherein the compound is a polyethylene or polypropylene monomethyl ether compound.

16. The synthetic phospholipid compound of claim 14 wherein the carboxyl is a $C_3$–$C_6$ carboxyl.

17. The synthetic phospholipid compound soy phosphatidylethanolamine succinyl polyethylene glycol monomethyl ether.

18. The synthetic phospholipid compound soy phosphatidylethanolamine glutaryl polyethylene glycol monomethyl ether.

* * * * *